United States Patent
Sun et al.

[11] Patent Number: 5,981,759
[45] Date of Patent: Nov. 9, 1999

[54] PROCESS FOR INDINAVIR INTERMEDIATE

[75] Inventors: Yongku Sun, Bridgewater, N.J.; Frank P. Gortsema, Pleasantville, N.Y.; Carl Leblond, Somerset; Kai Rossen, Westfield, both of N.J.

[73] Assignee: Merck & Co., Inc., Rahway, N.J.

[21] Appl. No.: 09/098,776

[22] Filed: Jun. 17, 1998

Related U.S. Application Data

[60] Provisional application No. 60/050,352, Jun. 20, 1997.

[51] Int. Cl.$^6$ .................................................. C07D 263/52
[52] U.S. Cl. .......................................................... 548/217
[58] Field of Search ............................................. 548/217

[56] References Cited

U.S. PATENT DOCUMENTS

| | | | |
|---|---|---|---|
| 5,413,999 | 5/1995 | Vacca et al. | 514/231.5 |
| 5,612,484 | 3/1997 | Askin et al. | 548/217 |
| 5,618,939 | 4/1997 | Askin et al. | 544/368 |
| 5,700,364 | 12/1997 | Rossen | 205/425 |
| 5,723,615 | 3/1998 | Rossen | 544/388 |
| 5,728,840 | 3/1998 | Askin et al. | 548/217 |

FOREIGN PATENT DOCUMENTS

| | | |
|---|---|---|
| 95/02583 | 1/1995 | WIPO . |
| 95/23797 | 9/1995 | WIPO . |

OTHER PUBLICATIONS

H. Masuda et al., "A New Synthetic Method of Preparing Iodohydrin and Bromohydrin Derivatives through in Situ Generation of Hypohalous Acids from H5IO6 and NaBrO3 in the Presence of NaHSO3", J. Org. Chem., 59, pp. 5550–5555 (1994).

K. Rossen et al., "Asymmetric Hydrogenation of Tetrahydropyrazines: Synthesis of (S)–Piperazine–2–tert–butylcarboxamide, and Intermediate in the Preparation of the HIV Protease Inhibitor indinavir", Tetrahedron Letters, vol. 36, No. 36, pp. 6419–6422 (1995).

D. Askin et al., "Highly Diastereoselective Reaction of a Chiral, Non–Racemic Amide Enolate with (S)–Glycidyl Tosylate. Synthesis of the Orally Active HIV–1 Protease Inhibitor L–735,524", Tetrahedron Letters, vol. 35, No. 5, pp. 673–676 (1994).

P. E. Maligres et al., "Diastereoselective Syn–Epoxidation of 2–Alkyl–4–Enamides to Expoxyamides: Synthesis of the Merck HIV–1 Protease Inhibitor Epoxide Intermediate", Tetrahedron Letters, vol. 36, No. 13, pp. 2195–2198 (1995).

Rossen et al., "Mechanistic Studies on the Diastereoselective Halohydroxylation of Gamma–Delta Unsaturated Carboxamides", Tetrahedron Letters, vol. 37, No. 38, pp. 6843–6846 (1996).

P. E. Maligres et al., "Cyclic Imidate Salts in Acyclic Stereochemistry: Diastereoselective Syn–Expoxidation of 2–Alkyl–4–Enamides to Epoxyamides", Tetrahedron Letters, vol. 52, No. 9, pp. 3327–3338 (1996).

Rossen et al., "A Highly Diastereoselective Electrochemical Epoxidation", Tetrahedron Letters, vol. 38, No. 5, pp. 777–778, 1997.

*Primary Examiner*—John M. Ford
*Attorney, Agent, or Firm*—Kenneth R. Walton; Melvin Winokur

[57] ABSTRACT

An intermediate in the synthesis of indinavir is prepared by iodohydroxylating an allyl acetonide by hypoiodous acid generated in situ from sodium hypochlorite and sodium iodide.

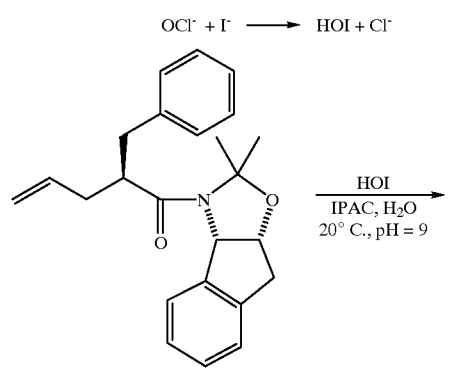

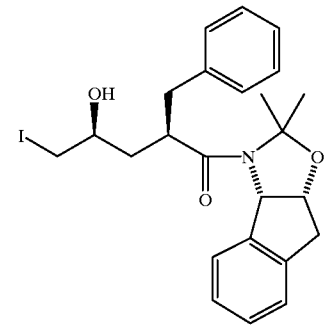

19 Claims, No Drawings

PROCESS FOR INDINAVIR INTERMEDIATE

This application claims the benefit of U.S. Provisional Application No. 60/050,352, filed Jun. 20,1997.

FIELD OF THE INVENTION

This invention is concerned with a novel process in which a d-g unsaturated carboxamide is halohydroxylated with efficient 1, 3 chirality transfer, producing halohydrin in high yield and high diastereoselectivity. More particularly, halohydroxylation of the olefin C=C double bond is achieved by treatment of the unsaturated carboxamide with hypohalous acid ($HOX^1$) generated in situ via co-addition of an alkali metal hypohalite (MOX) and an alkali metal halide ($MX^1$) wherein M is sodium or potassium, $X^1$ is I or Br, X is Cl when $X^1$ is Br and X is Cl or Br when $X^1$ is I.

BACKGROUND OF THE INVENTION

The novel process is particularly useful for the preparation of an intermediate in the synthesis of the protease inhibitor, indinavir sulfate (CRIXIVAN®) which is known to be useful in the prevention of infection by HIV (human immunodeficiency virus), the treatment of infection by HIV and the treatment of the resulting acquired immune deficiency syndrome (AIDS).

Previously, the synthesis of indinavir and related compounds was accomplished via a 12-step procedure which employed a hydroxy protected dihydro-5(S)-hydroxymethyl-3(2H) furanone which was alkylated, and involved replacement of an alcohol leaving group on the alkylated furanone with a piperidine moiety. The coupled product was then hydrolyzed to open the furanone ring into a hydroxy acid moiety, and the acid was ultimately coupled to 2(R)-hydroxy-1(S)-aminoindane. This procedure is described in U.S. Pat. No. 5,413,999. The extreme length of this route (12 steps), renders this process time consuming and labor intensive, and it requires the use of many expensive reagents and an expensive starting material. A route requiring fewer reaction steps and reagents would provide desirable economical and time-saving benefits.

A modified route to indinavir and related compounds was also shown in U.S. Pat. No. 5,413,999 based on the diastereoselective alkylation of the enolate derived from N-(2(R)-hydroxy-1(S)-indan-N,O-isopropylidenyl) -3-phenylpropaneamide, in which the $C_3$–$C_5$ three-carbon unit was introduced as an allyl group and later oxidized. Some problems with this route are: (a) four steps are necessary to effect the introduction of the three carbon glycidyl fragment, (b) highly toxic $OsO_4$ is used in the process and (c) low diastereoselectivity is obtained in the dihydroxylation step. Thus, a desirable process would directly introduce the three carbon unit in the correct chiral oxidized form.

Furthermore, the synthesis of the chiral piperazine intermediate was effected from 2-pyrazinecarboxylic acid in a 6 step procedure and required the use of expensive reagents such as BOC-ON and EDC. A shorter route to the piperazine intermediate which also does not use expensive reagents would thus be desired. Moreover, during the synthesis of the chiral piperazine intermediate, both the desired (S)-piperazine carboxylate enantiomer (i.e., the precursor to the 2(S)-carboxamide piperazine intermediates) and the undesired (R)-enantiomer are formed requiring separation of the desired (S)-enantiomer which is then carried on to ultimately form indinavir. In the absence of practical methodology for converting the (R)-antipode to the (S)-antipode, it was discarded as waste, thus limiting the possible efficiency of this step to 50%.

More recently, a shorter route for preparing the compounds disclosed in U.S. Pat. No. 5,413,999 and in particular indinavir, was found. In this newer route, 1-((R)-2',3'-Epoxypropyl-(S)-2-tert-butylcarbonyl-piperazine is prepared and reacted with N-(2(R)-hydroxy-1(S)-indan-N,O-isopropylidene-yl) -3-phenylpropaneamide to give the coupled product.

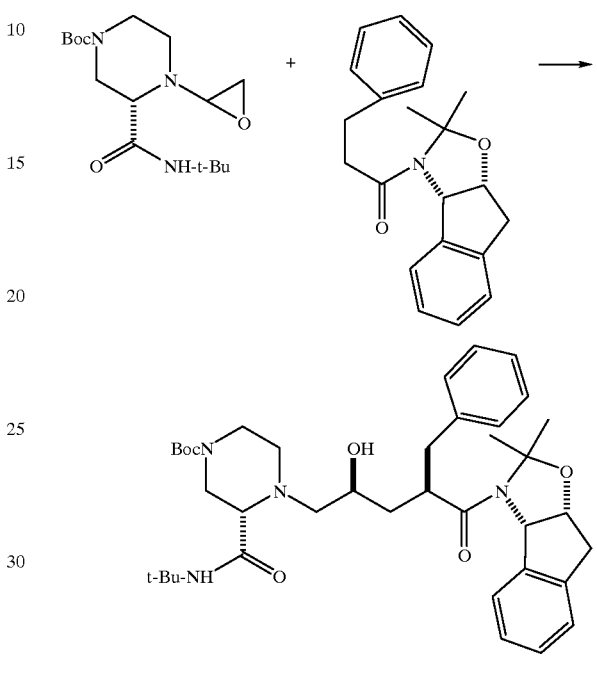

After removal of the BOC protecting group from the piperazine nitrogen, the unprotected piperazine compound is then reacted with 3-picolyl chloride to form indinavir.

Still more recently, a novel process somewhat similar to the presently claimed process for preparing the same intermediate as in the present process was claimed in WO 95/23797. That process is as follows:

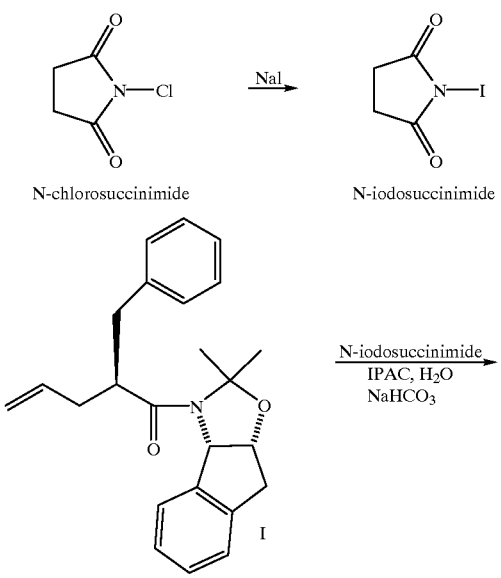

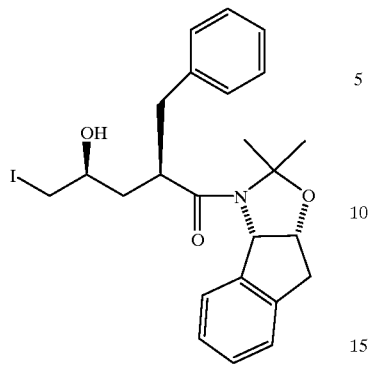

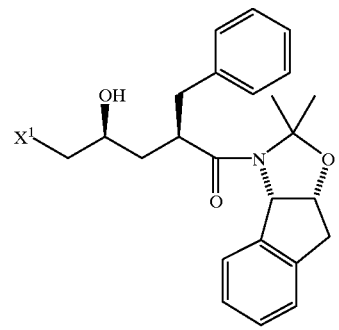

which comprises treating an allyl acetonide compound of structural formula I

In that process N-chlorosuccinimide (NCS) is used as the oxidant for iodohydrination of allyl acetonide intermediate I. With the present invention, NaOCl is used as the oxidant which has several advantages. First of all, NaOCl is a much less expensive raw material as compared with NCS. Secondly, NCS is a sticky solid which is difficult to handle effectively in the manufacturing process. On the other hand, NaOCl (aqueous) is a solution which can be easily handled by a liquid pump. Thirdly, a large amount of succinimide is present in the waste aqueous stream in the NCS process, which would hinder the recovery of iodide from the waste stream. The NaOCl process of the present invention eliminates succinimide as a side product, hence facilitating the recovery of iodide from the waste stream.

Halohydrination of Compound I can also be accomplished electrochemically by passing a current through a solvent system containing the substrate, I, and sodium iodide or sodium bromide, using carbon felt as electrodes (Tetrahedron Lett. 1997, 38, 777). Using a biphasic solvent system of isopropyl acetate/water, the iodohydrin can be produced, but with a low yield of 69%. Using acetonitrile/water as solvent, the bromohydrin can be produced with 86% yield and a relatively low diastereoselectivity of 88%de.

The novel process of the present invention is clearly superior to other known processes for the preparation of the halohydrin product by virtue of higher physical yields, greater diastereoselectivity and/or ease of isolation and waste disposal.

SUMMARY OF THE INVENTION

The present invention provides a process for forming a compound of structural formula II:

in an organic solvent with an aqueous solution of an alkali metal hypohalite of formula MOX and an aqueous solution of an alkali metal halide of formula $MX^1$ wherein M is potassium or sodium, $X^1$ is I or Br, X is Cl when $X^1$ is Br and X is Cl or Br when $X^1$ is I. The alkali metal, M, in the alkali metal hypohalite MOX can be the same or different from the alkali metal, M, in the alkali metal halide $MX^1$.

In one embodiment of the invention, the process is conducted with vigorous stirring.

In a class of the invention, the process is conducted at a temperature about 10 to about 50° C., preferably about 15 to about 30° C., more preferably, about 20 to about 30° C., and most preferably, about 20° C.

In a subclass of the invention, the process is conducted at a pH about 6 to about 11, preferably, about 8 to about 10, and most preferably, about 9 to about 9.5.

Illustrative of the invention is the process wherein M is sodium, X is Cl and $X^1$ is I.

An illustration of the invention is the process wherein the organic solvent is a lower alkanoic acid $C_{1-4}$ alkyl ester, preferably, isopropyl acetate.

Exemplifying the invention is the process wherein the MOX solution and the $MX^1$ solution are added to the allyl acetonide I simultaneously. Alternatively, the MOX solution and the $MX^1$ solution are added to the allyl acetonide I sequentially by adding $MX^1$ to the allyl acetonide first, followed by a slow addition of MOX to the batch.

An example of the invention is the process wherein the ratio of MOX:$MX^1$ is about 1:1, but may vary by about 35% either way. Preferably, the ratio of MOX:$MX^1$ is about 1:1.

Further illustrating the invention is the process wherein the NaOCl and NaI are added to the allyl acetonide I simultaneously. In a particularly preferred process, the ratio of the NaOCl:NaI is about 1:1, but may vary by about 35% either way (preferably, the ratio of MOX:MX¹ is about 1:1) during the simultaneous addition; the temperature is about 10 to about 50° C., preferably about 15 to about 30° C., more preferably, about 20 to about 30° C, and most preferably, about 20° C.; the pH is about 6 to about 11, preferably, about 8 to about 10, and most preferably, about 9 to about 9.5; and the solvent is a lower alkanoic acid $C_{1-4}$ alkyl ester, preferably, isopropyl acetate.

DETAILED DESCRIPTION

The novel process of this invention comprises halohydrination of the allylic group of I by treatment of I with aqueous alkali metal hypohalite and an alkali metal halide which can be depicted as follows:

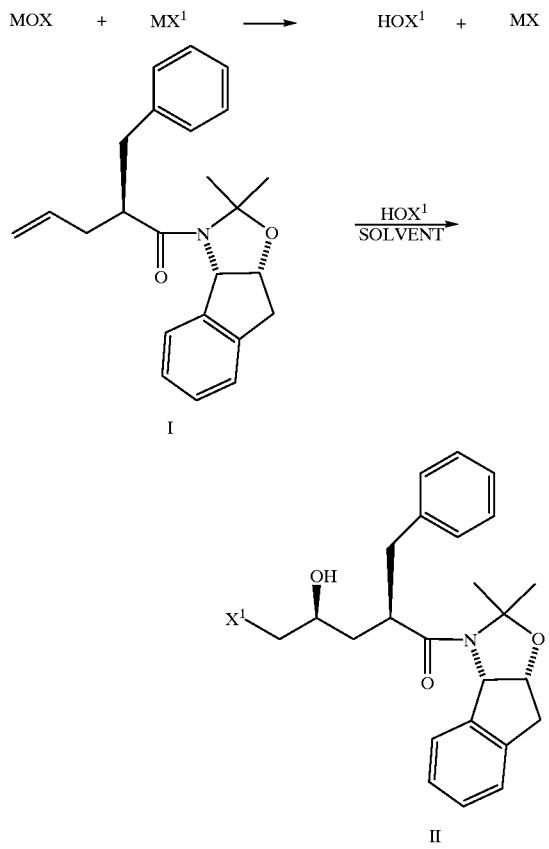

wherein M is sodium or potassium, $X^1$ is I of Br, X is Cl when $X^1$ is Br and X is Cl or Br when $X^1$ is I.

In the process of the present invention, the alkali metal, M, in the alkali metal hypohalite MOX can be the same or different from the alkali metal, M, in the alkali metal halide $MX^{1.}$ Thus, for example, MOX can be NaOX and $MX^1$ can be $NaX^1$; MOX can be KOX and $MX^1$ can be $KX^{1;}$ MOX can be NaOX and $MX^1$ can be $KX^{1;}$ or MOX can be KOX and $MX^1$ can be $NaX^1$.

In this process, a highly active halohydroxylation reagent, a hypohalous acid ($HOX^1$), is generated in situ in the reactor by two means. The first one is a co-addition of an alkali metal hypohalite, MOX, especially NaOCl and an alkali metal halide, $MX^{1,}$ especially NaI. The second one is a slow addition of an alkali metal hypohalite, MOX, especially NaOCl to a batch containing I and an alkali metal halide, $MX^{1,}$ especially NaI. The $HOX^1$ thus generated reacts rapidly with the allylic group of I producing the halohydrin product II. The first method produces iodohydrin with less impurity and higher yield, and is hence the preferred method.

The concentration of MOX feed solution is about 1–22%, preferably about 8–17% and most preferably about 13–15% by weight.

The concentration of the $MX^1$ (i.e., sodium or potassium halide) feed solution is any concentration up to the saturation point at room temperature, e.g., about 1–60%, preferably about 30–60%, more preferably about 50–60% and most preferably about 57% by weight.

The molar ratios of the two reagents, MOX and $MX^1$, should be roughly 1:1 but can vary by about 35% either way.

The starting concentration of the allylic compound I in the reactor is up to about 160 g(L in an organic solvent. Suitable solvents include, but are not limited to, a lower alkanoic acid $C_{1-4}$ alkyl ester such as ethyl propionate, n-propyl acetate, butyl acetate, ethyl acetate, methyl acetate or preferably isopropyl acetate (IPAC), acetonitrile, or halogenated solvents such as methylene chloride or chloroform.

In the case of co-addition, the addition of the two reagents takes about 20–120 minutes, preferably about 30–90 minutes and most preferably about 45–60 minutes.

In the case of addition of $MX^1$ to a batch containing MOX and I, the addition takes about 20–120 minutes, preferably about 30–90 minutes and most preferably about 45–60 minutes.

The agitation should be vigorous to maximize the liquid-liquid mixing efficiency. The term "vigorous stirring," as used herein, refers to sufficient stirring of the reaction mixture to ensure that no phase separation is visible to the naked eye between the aqueous and organic phases. That is, although the aqueous and organic phases present in the reaction mixture still exist, the stirring is sufficient (i.e., fast enough) so that no visible phase separation can be detected by the naked eye.

The temperature of the reaction should be at about 10–50° C., preferably about 15–30° C. and most preferably about 20–30° C.

The batch pH of the reaction mixture should be controlled at about 6–11, preferably about 8–10 and most preferably about 9.0–9.5. Addition of dilute acid and/or base as needed serves adequately to maintain this optimum pH. Additionally, a buffer may be used to help with pH control of the batch. Any buffer system may be employed that has a buffering range between about pH 8–10 such as (a) sodium carbonate-sodium bicarbonate (by adding $NaHCO_3$), (b) phthalic acid-potassium dihydrogen phthalate, (c) potassium dihydrogen phosphate-dipotassium hydrogen phosphate and (d) boric acid-sodium borate. Acids which may be employed in pH control include sulfuric, hydrochloric, acetic, trifluoroacetic and dilute nitric acid.

Specifically, in the case of co-addition for iodohydroxylation of the allyl acetonide I, sodium hypochlorite and sodium iodide solutions are pumped concurrently, slowly and separately into a reactor containing an isopropyl acetate solution of the allyl acetonide so that the relative molar ratio of NaOCl : NaI : allyl acetonide is about 1.56: 1.4: 1, under vigorous agitation, while the batch pH and temperature are controlled at about 9 and 20° C, respectively. A typical conversion of allyl acetonide at the end of the addition is over 99.5% and assay yield is about 95%. HPLC analysis generally shows that the iodohydrin II is produced with a high diastereoselectivity of about 96% (98:2) comparable to results obtained with the previously known N-iodosuccinimide process.

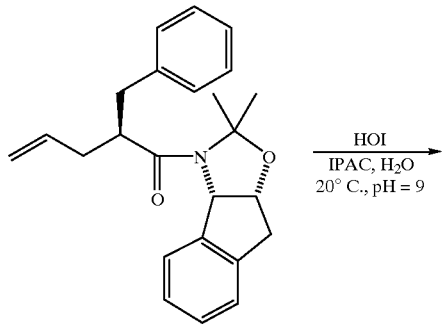

-continued

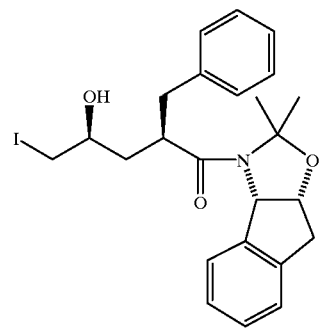

The above discussion has dealt specifically with sodium iodide, but similar considerations and results would pertain employing sodium bromide.

The successful complete conversion of the allyl acetonide I to iodohydrin II is surprising, considering that HOI is highly unstable and short-lived. The key to the success is the carefully designed operational procedure that minimizes the "annihilation" of the active HOI and maximizes the chance of reaction between HOI and I to iodohydrin.

The conversion of the product of the novel process of this invention into indinavir is fully described in WO 95/23797 and involves a process which can be depicted as follows:

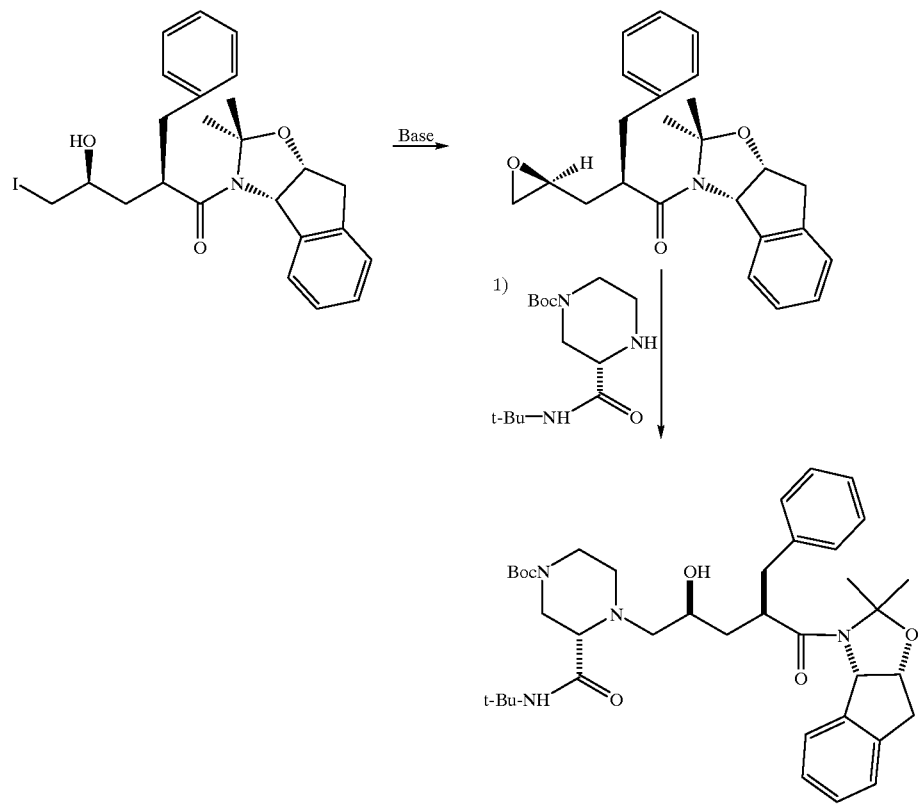

-continued

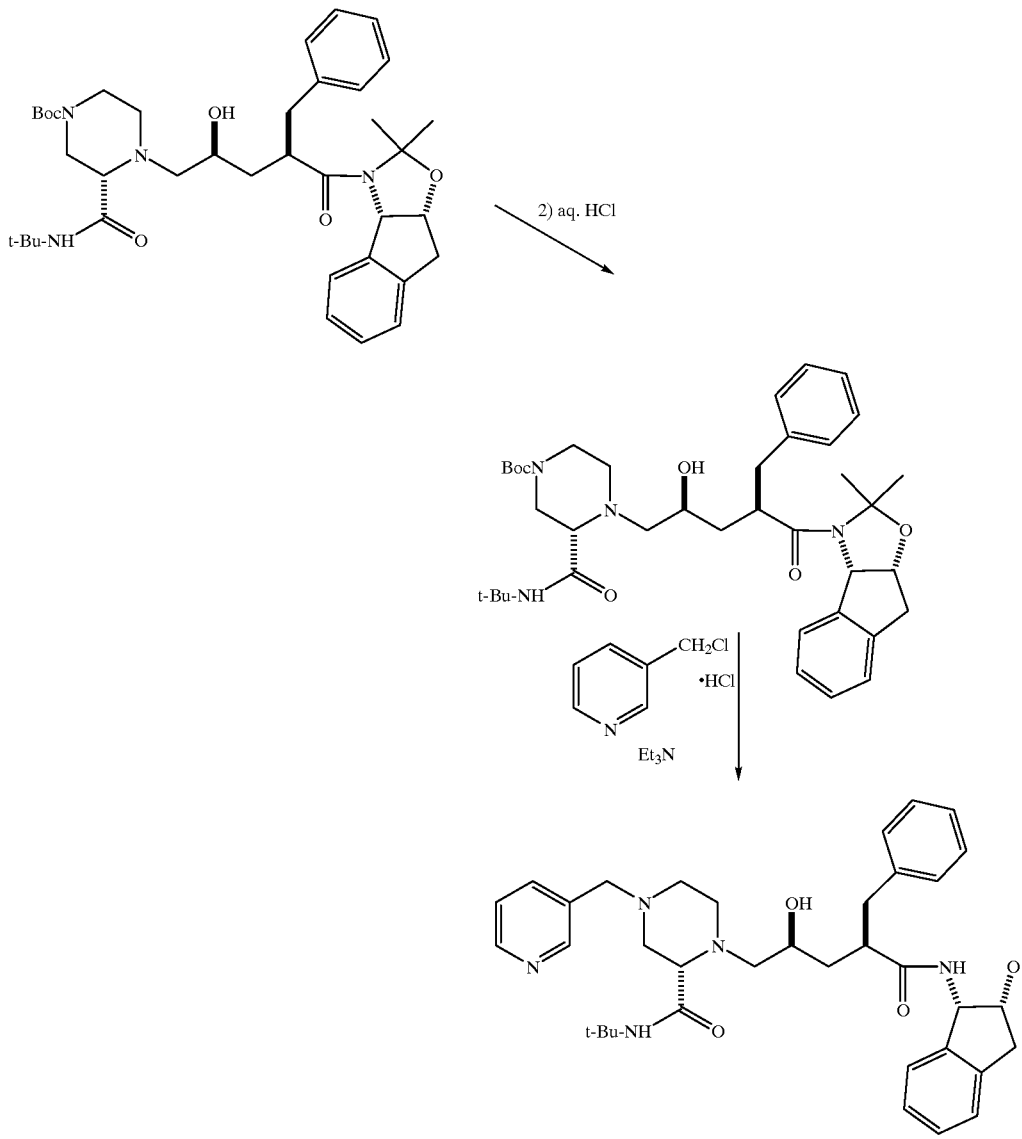

The following examples are provided to further define the invention without, however, limiting the invention to the particulars of these examples.

EXAMPLE 1

The following example illustrating the use of sodium hypochlorite as described in the above discussion was carried out in a Mettler RC-1 reaction calorimeter (reactor volume: 1L) which provides computer control over the batch pH and temperature, and liquid dosing control functions. Other reaction systems in which the batch pH and temperature as well as liquid dosing can be controlled can also be used.

To the top charge opening in the reactor was added 250 ml of allyl acetonide I in isopropyl acetate having an assay of 135 g/l (0.0934 mole), followed by the addition of 151 ml of deionized water and 0.5 g of $NaHCO_3$. The reactor stirrer was set to 600 rpm and the reactor temperature adjusted to 20° C. while purging the system with nitrogen. A pH control probe was inserted into the reactor and the system was purged with nitrogen to remove air.

To the reactor was added 1.56 equivalents (83.12 g) of 13.02 wt. % sodium hypochlorite solution and 1.4 equivalents (34.41 g, 20.25 ml) of 57% NaI solution over a time interval of 46.7 minutes. The NaI solution was added using a syringe pump at an addition rate of 0.427 ml/min. The NaOCl solution was added by means of a Prominent pump, adjusted to provide a uniform addition rate. Concurrent with the addition of the NaOCl and NaI solution, $H_2SO_4$ was added at a rate such that the reactor contents were maintained at a pH of 9.0. The addition was conducted suprasurface, and the three addition tubings were positioned in the reactor vessel at maximum separation from one another. The reaction was continued for a period of 10 minutes after complete addition of the NaOCl and NaI solutions. At the end of this time, samples were taken for LC analysis. The conversion was usually greater than 99.5% at this point. Another 0.25 eq of NaOCl was added over a period of 20 minutes to ensure complete conversion of allyl acetonide I, followed by quenching the reaction mixture with 20% $Na_2SO_3$ solution.

The products were identified by LC and the conversion of I was nearly 100%. The assay yield of 2R,4RS-iodohydrin determined by exact measurement of the final volume of the organic phase, and LC analysis of the concentration was determined to be 95%. The diastereomeric excess of the 2R,4S-iodohydrin II (X=I) was measured to be 96%.

EXAMPLE 2

The same reactor system was used as that in Example 1.

To the top charge opening in the reactor was added 250 ml of allyl acetonide I in isopropyl acetate having an assay of 142 g/l, followed by the addition of 1.8 eq. of solid NaI and 151 ml of deionized water and 0.5 g of $NaHCO_3$. The reactor stirrer was set to 600 rpm and the reactor temperature adjusted to 20° C. while purging the system with nitrogen. A pH control probe was inserted into the reactor and the system was purged with nitrogen to remove air.

To the reactor was added 2.0 equivalents of NaOCl (13 Wt %) over 60 minutes. The NaOCl solution was added by means of a Prominent pump, adjusted to provide a uniform addition rate. Concurrent with the addition of the NaOCl solution, $H_2SO_4$ was added at a rate such that the reactor contents were maintained at a pH of 9.0. The reaction was continued for a period of 10 minutes after complete addition of the NaOCl. At the end of this time, samples were taken for LC analysis. The conversion was greater than 99% at this point. The batch was quenched by adding to the reaction mixture 20% $Na_2SO_3$ solution.

The products were identified by LC and the conversion of I was greater than 99.5%. The assay yield of 2R,4RS-iodohydrin determined by exact measurement of the final volume of the organic phase, and LC analysis of the concentration was determined to be 88%, slightly lower than what was observed in Example I due to formation of greater amount of impurity. The diastereomeric excess of the 2R,4S-iodohydrin II (X=I) was measured to be 96%.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A process for forming a compound of structural formula II:

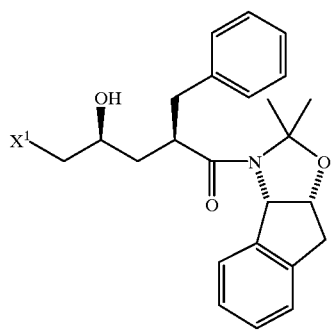

II which comprises treating an allyl acetonide compound of structural formula I

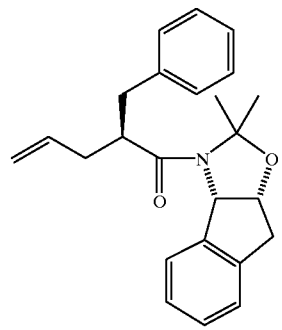

I in an organic solvent with an aqueous solution of an alkali metal hypohalite of formula MOX and an aqueous solution of an alkali metal halide of formula $MX^1$ wherein M is potassium or sodium, $X^1$ is I or Br, X is Cl when $X^1$ is Br and X is Cl or Br when $X^1$ is I; and wherein (i) the MOX solution and the $MX^1$ solution are added to the allyl acetonide I simultaneously or (ii) the MOX solution and the $MX^1$ solution are added to the allyl acetonide I sequentially by adding $MX^1$ to the allyl acetonide first, followed by a slow addition of MOX to the batch.

2. The process of claim 1, wherein the process is conducted with vigorous stirring.

3. The process of claim 2, wherein the process is conducted at a temperature about 10 to about 50° C.

4. The process of claim 2, wherein the process is conducted at a pH about 6 to about 11.

5. The process of claim 2, wherein M is sodium, X is Cl and $X^1$ is I.

6. The process of claim 2, wherein the organic solvent is a lower alkanoic acid $C_{1-4}$ alkyl ester.

7. The process of claim 6, wherein the organic solvent is isopropyl acetate.

8. The process of claim 1, wherein the ratio of $MOX:MX^1$ is about 1:1, but may vary by about 35% either way.

9. The process of claim 8, wherein the ratio of $MOX:MX^1$ is about 1:1.

10. The process of claim 5, wherein the NaOCl and NaI are added to the allyl acetonide I simultaneously.

11. The process of claim 10, wherein the ratio of the NaOCl:NaI is about 1:1, but may vary by about 35% either way.

12. The process of claim 11, wherein the ratio of the NaOCl: NaI is about 1:1.

13. The process of Claim 11, wherein the process is conducted at a temperature about 10 to about 50° C.

14. The process of claim 13, wherein the process is conducted at a pH about 6 to about 11.

15. The process of claim 14, wherein the organic solvent is a lower alkanoic acid $C_{1-4}$ alkyl ester.

16. The process of claim 15, wherein the organic solvent is isopropyl acetate.

17. The process of claim 15, wherein the process is conducted at a temperature about 15 to about 30° C.

18. The process of claim 17, wherein the process is conducted at a pH about 8 to about 10.

19. The process of claim 6, wherein M is sodium, X is Cl and $X^1$ is I.

* * * * *